US006365141B2

(12) United States Patent
Nye et al.

(10) Patent No.: US 6,365,141 B2
(45) Date of Patent: *Apr. 2, 2002

(54) METHOD OF USING AN ARALKYLSILOXANE

(75) Inventors: Susan A. Nye, Feura Bush; Virginia V. Powell, East Nassau, both of NY (US)

(73) Assignee: General Electric Company, Pittsfield, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/187,653

(22) Filed: Nov. 6, 1998

(51) Int. Cl.$^7$ ................................................ A61K 7/06
(52) U.S. Cl. .................................... 424/70.12; 424/70.1
(58) Field of Search ............................. 424/70.12, 70.1

(56) References Cited

U.S. PATENT DOCUMENTS

| 3,088,964 A | | 5/1963 | Ryan |
| 3,839,384 A | | 10/1974 | Morehouse |
| 4,053,581 A | * | 10/1977 | Pader et al. |
| 5,160,730 A | | 11/1992 | Dubief et al. |
| 5,300,669 A | | 4/1994 | Akamatsu |
| 5,384,383 A | | 1/1995 | Legrow et al. |
| 5,415,854 A | * | 5/1995 | Forestier et al. ............... 424/59 |
| 5,441,667 A | * | 8/1995 | Tonomura et al. ...... 252/174.15 |
| 5,531,986 A | | 7/1996 | Shevade et al. |
| 5,554,313 A | * | 9/1996 | Chandler ..................... 510/121 |
| 5,674,478 A | * | 10/1997 | Dodd et al. ................. 424/70.1 |
| 5,811,085 A | * | 9/1998 | Halloran ..................... 424/70.2 |
| 5,830,486 A | * | 11/1998 | Nanba et al. ................ 424/401 |

FOREIGN PATENT DOCUMENTS

| EP | 0 549 223 | 6/1993 |
| EP | 0 756 865 | 2/1997 |

OTHER PUBLICATIONS

Functional Polysiloxane Polysiloxanes containing Choromethylphenethyl Groups, Eur. Polym. J. vol. 30, No. 3, pp. 309–312, 1994.

Addition of Silicon Hydrides to Olefinic Double Bonds. IV. The Addition to Styrene and α–Methylstyrene; John W. Ryan and John L. Speier; vol. 24.

* cited by examiner

Primary Examiner—Thurman K. Page
Assistant Examiner—Amy E Pulliam

(57) ABSTRACT

A method of using of an aralkylalkylsiloxane includes adding the aralkylsiloxane as a component in a personal care composition, in an amount effective to enhance one or more properties, such as shine, lubricity and visual masking of inorganic components, of the personal care composition.

4 Claims, No Drawings

METHOD OF USING AN ARALKYLSILOXANE

FIELD OF THE INVENTION

The invention relates to the use of certain siloxane compounds, more particularly to the use of certain aralkylsiloxane compounds.

BRIEF DESCRIPTION OF THE RELATED ART

The use of phenyltrimethicone in personal care compositions, for example, skin lotions, antiperspirants, hair care products to enhance shine, lubricity and/or visual masking of inorganic components, is known. Typical methods for making phenyltrimethicone, such as for example, by cohydrolysis of phenyltrichlorosilane and chlorotrimethylsilane may introduce impurities, such as for example, side products and catalyst residues, into the phenyltrimethicone product which are undesirable in the context of using the phenyltrimethicone product as a component in a personal care composition.

SUMMARY OF THE INVENTION

In a first aspect, the present invention is directed to a method of using of an aralkylsiloxane, comprising adding the aralkylsiloxane as a component in a personal care composition, in an amount effective to enhance one or more properties of the personal care composition. For example, the aralkylsiloxane enhances the shine, emolliency and lubricity of personal care compositions and aids in visually masking inorganic components of such compositions.

In a second aspect, the present invention is directed to a method for making an aralkyl siloxane, comprising contacting a silylhydride-functional polysiloxane with a terminally unsaturated arylalkene under hydrosilylation conditions. Aralkylsiloxanes made by the preferred process exhibit a low, preferably an undetectably low, level of impurities and thus allow the amount of impurities introduced into the personal care composition by addition of such aralkylsiloxanes to be minimized.

In a third aspect, the present invention is directed to a method for making an improved personal care composition, said personal care composition being an analog of a first personal care composition that contains phenyltrimethicone as a component thereof, comprising making a personal care composition analogous to the first personal care composition wherein an aralkylsiloxane is substituted for the phenyltrimethicone of the first personal care composition.

DETAILED DESCRIPTION OF THE INVENTION

In a preferred embodiment, the personal care composition comprises, based on 100 parts by weight ("pbw") of the personal care composition, from about 0.5 pbw to about 50 pbw, more preferably from about 1 pbw to about 30 pbw, still more preferably from about 2 pbw to about 20 pbw, of the aralkylalkylsiloxane.

Aralkylsiloxanes that are suitable as the aralkylsiloxane component of the present invention are those comprising one or more compounds according to formula (I):

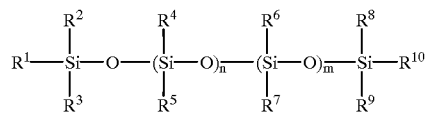

(I)

wherein:
$R^1$, $R^2$, $R^3$, $R^4$, $R^5$, $R^8$ and $R^9$ and $R^{10}$ are each independently H, alkyl, more preferably $(C_1-C_6)$alkyl, haloalkyl, more preferably halo$(C_1-C_6)$alkyl, aryl or aralkyl,
$R^6$, $R^7$ are each independently H, alkyl, more preferably $(C_1-C_6)$alkyl, haloalkyl, more preferably halo$(C_1-C_6)$alkyl, or aryl; n and m are each independently integers from 0 to 6, provided that $(n+m) \geq 1$, preferably $1 \leq (n+m) \leq 8$, still more preferably $1 \leq (n+m) \leq 4$ and provided that at least one substituent group of the compound of formula (I) is aralkyl; or of formula (II):

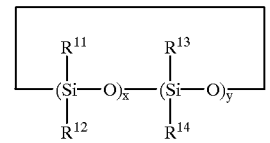

(II)

wherein:
$R^{11}$ and $R^{12}$ are each independently H, alkyl, more preferably $(C_1-C_6)$alkyl, haloalkyl, more preferably halo$(C_1-C_6)$alkyl, aryl or aralkyl; $R^{13}$ and $R^{14}$ are each independently H, alkyl, more preferably $(C_1-C_6)$alkyl, haloalkyl, more preferably halo$(C_1-C_6)$alkyl, or aryl; x and y are each independently integers from 0 to 6, provided that $3 \leq (x+y) \leq 10$, preferably $4 \leq (x+y) \leq 6$, and provided that at least one substituent group of the compound of formula (II) is aralkyl.

As used herein, the term "$(C_1-C_6)$alkyl" means a linear or branched alkyl group containing from 1 to 6 carbons per group, such as, for example, methyl, ethyl, propyl, isopropyl, n-butyl, iso-butyl, sec-butyl, tert-butyl, pentyl, hexyl, preferably methyl.

As used herein, the term "halo$(C_1-C_6)$alkyl" means a linear or branched alkyl group containing from 1 to 6 carbons per group that is substituted with one or more halo substituents, such as, for example, chloromethyl, trifluoromethyl.

As used herein, the term "aryl" means a monovalent unsaturated hydrocarbon ring system containing one or more aromatic rings per group, which may optionally be substituted on the one or more aromatic rings, preferably with one or more groups selected from amino, nitro, $(C_1-C_6)$alkyl, and which, in the case of two or more rings, may be fused rings, including, for example, phenyl, 2,4,6-trimethylphenyl, 2-isopropylmethylphenyl, 1-pentalenyl, naphthyl, anthryl, preferably phenyl.

As used herein, the term "aralkyl" means an aryl derivative of an alkyl group, preferably a $(C_2-C_6)$alkyl group, wherein the alkyl portion of the aryl derivative may, optionally, be interrupted by an oxygen atom, such as, for example, phenylethyl, phenylpropyl, 2-(1-naphthyl)ethyl, preferably phenylpropyl, phenyoxypropyl, biphenyloxypropyl.

In a highly preferred embodiment, the aralkylsiloxane comprises a compound according to formula (I), wherein $R^1$ and $R^{10}$ are each aralkyl, more preferably phenylpropyl, $R^2$, $R^3$, $R^6$, $R^7$, $R^8$ and $R^9$ are each ($C_1$–$C_6$) alkyl, more preferably methyl, n is 0 and $2 \leq m \leq 5$,, more preferably n is 0 and m is 3. In a very highly preferred embodiment, the aralkylsiloxane comprises α,ω-bis(2-phenylpropyl) siloxane.

In a preferred embodiment, the aralkylsiloxane comprises a compound according to formula (I), wherein $R^1$, $R^2$, $R^3$, $R^4$, $R^6$, $R^7$, $R^8$, $R^9$ and $R^{10}$ are each ($C_1$–$C_6$) alkyl, preferably methyl, $R^5$ is aralkyl, more preferably phenylpropyl, , n is 1 or 2 and $1 \leq m \leq 8$, more preferably, n is 1 and m is 2.

In a preferred embodiment, the aralkyl siloxane comprises a compound according to the structural formula (II), wherein $R^{11}$, $R^{13}$ and $R^{14}$ are each ($C_1$–$C_6$) alkyl, preferably methyl, $R^{12}$ is aralkyl, more preferably phenylpropyl, $1 \leq x \leq 4$ and $2 \leq y \leq 10$, more preferably x is 1 and y is 4.

In a highly preferred embodiment, the aralkyl content of the aralklysiloxane is selected to provide a refractive index of from 1.40 to 1.50, more preferably from about 1.44 to 1.48, at 25° C. In a highly preferred embodiment, the aralkylsiloxane comprises, based on the molecular weight of the aralkylsiloxane, from about 25 to about 65 percent by weight ("wt %"), more preferably from about 30 to about 50 wt % and still more preferably from about 33 to about 45 wt %, of one or more aralkyl substituent groups.

Suitable aralkylsiloxane can be made by known methods, see, for example, U.S. Pat. Nos. 3,088,964 and 5,300,669 and 5,384,383, the disclosures of which are each incorporated herein by reference.

In a preferred embodiment, the aralkylsiloxane is made by contacting a silylhydride-functional polysiloxane with an terminally unsaturated arylalkene, such as for example, styrene or 2-phenylpropene, under hydrosilylation conditions, preferably in the presence of a solid hydrosilylation catalyst. In a preferred embodiment, the solid hydrosiliylation catalyst comprises a catalytically active metal, such as for example, platinum, supported on an inert support, such as for example, alumina. Preferably, the aralkylsiloxane product exhibits a hydride content of less than 100 parts per million ("ppm"), based on the weight of aralkylsiloxane. The catalyst and excess arylalkene may be easily removed form the product mixture to yield an aralkylsiloxane having a low to undetectably low content of impurities. In a preferred embodiment, the solid catalyst is removed from the aralkylsiloxane product by filtration. Excess arylalkene may be removed by heating the product mixture by vacuum stripping the aralkylsiloxane.

The personal care applications in which an aralkylalkylsiloxane may be employed include, but are not limited to, deodorants, antiperspirants, skin lotions, moisturizers, hair care products such as shampoos, hair conditioners, mousses, hair sprays and styling gels, protective compositions such as sunscreens, skin treatments and anti-aging products, color cosmetics such as lipsticks, foundations, blushes, makeup, and mascaras; and other cosmetic formulations, as well as drug delivery systems for topical application of medicinal compositions that are to be applied to the skin. Suitable personal care compositions are made by combining, according to methods known in the art, one or more of the above components with an aralkylalkylsiloxane.

In a preferred embodiment, suitable for example, as an after bath oil composition, the personal care composition of the present invention comprises a mineral oil and an aralkylsiloxane.

In a preferred embodiment, suitable for example, as a hair conditioner composition, the personal care composition of the present invention comprises a suitable solvent, such as for example, isododecane, isohexadecane or cyclomethicone and an aralkylsiloxane.

In a preferred embodiment, suitable for example, as a skin care composition, the personal care composition of the present invention comprises the aralkylsiloxane and a non-aqueous medium, comprising for example one or more of organic oils, such as sunflower seed oil and octyldodecylneopentanoate, and silicone oils, such as dimethicone and cyclomethicone, or with an aqueous medium, preferably in the form of an emulsion. Preferably the skin care composition further comprises one or more suitable emulsifiers, such as, for example, fatty acid esters, sorbitan derivatives such as sorbitan sesquioleate, sorbitan oleate, sorbitan isostearate, polyglyceryl-3 oleate, alkoxylated alcohols such as laureth-4, laureth-7, deceth-12, steareth-10, hydroxylated or alkoxylated derivatives of silicone compounds such as dimethicone copolyol, cetyl dimethicone copolyol, and lauryl methicone copolyol and glyceryl esters such as polyglyceryl-4-isostearyl.

In a preferred embodiment, suitable as an anti-perspirant composition the personal care composition of the present invention comprises one or more active anti-perspirant agents, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, and an aralkylsiloxane.

In a preferred embodiment, suitable, for example, as a sunscreen composition, the personal care composition of the present invention comprises one or more absorbing or blocking agents for ultraviolet radiation, such as, for example, titanium dioxide, p-aminobenzoic acid and oxybenzone sunscreens, such as benzophenone-3 and an aralkylsiloxane. In a preferred embodiment, the sunscreen composition is in the form of an aqueous emulsion, further comprising water and one or more emulsifiers.

The personal care composition of the present invention may, optionally, further contain such known components as, for example, emollients, moisturizers, humectants, pigments, colorants, fragrances, biocides, preservatives, exfoliants, hormones, enzymes, medicinal compounds, anti-microbial agents, anti-fungal agents, vitamins, salts, electrolytes, alcohols, polyols, absorbing or blocking agents for ultraviolet radiation, botanical extracts, surfactants, emulsifiers, silicone oils, organic oils, waxes, thickening agents such as, for example, acrylic polymers, fumed silica or hydrated silica, clays, such as, for example, bentonite, and organo-modified clays.

EXAMPLE 1

A reaction vessel was charged with 450 pbw of an equilibrated hydride-terminated siloxane oligomer having an average structure according to formula (III):

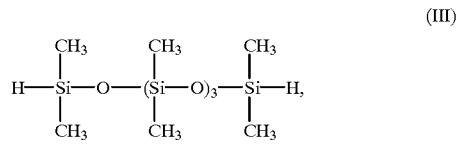

(III)

0.15 pbw of 5 wt % platinum on alumina. The reaction mixture was heated to 130° C. at which point the addition of 292 pbw (α-methyl styrene was begun. The progress of the reaction was followed by gasiometric analysis of the remaining hydride. After 2 hours at 130° C., the hydride level had been reduced to 62 parts per million. Excess α-methyl styrene was then removed by heating the contents of the reaction vessel to 150° C. under reduced pressure with a nitrogen sparge and the catalyst was removed by filtration to yield a clear, colorless liquid having a refractive index of 1.4650 at 25° C.

EXAMPLE 2 AND COMPARATIVE EXAMPLES C1 AND C2

The solid stick antiperspirant compositions of Example 2 and Comparative Examples C1 and C2 were made by combining the components in the relative amounts, expressed in pbw, set forth below in Table I.

Each of the compositions was made by: (i) mixing the siloxane component(s), that is, the cyclopentasiloxane and, as applicable, the phenyl trimethicone or α,ω-bis(2-phenylpropyl)siloxane, with the stearyl alcohol component, (ii) adding the aluminum zirconium chlohydex gly, talc and glyceryl stearate and PEG-100 stearate components, (iii) heating the mixture of components to 75° C. and stirring with moderate agitation until the waxes are melted, (iv) adding melted hydrogenated castor oil to the mixture and stirring for 15 minutes, and (v) cooling the mixture to 55° C. and pouring the mixture into containers.

Each of the compositions was applied to skin and evaluated for the amount of white residue visible on the skin after application. The results of the evaluation are indicated in TABLE 1, with a "+" indicating that white residue was visible and a "−" indicating that no white residue was visible. Neither Example 2 nor Comparative Example C2 left a visible white residue.

TABLE 1

|  | 2 | C1 | C2 |
|---|---|---|---|
| Cyclopentasiloxane | 40 | 50 | 40 |
| Phenyl trimethicone | — | — | 10 |
| α,ω-bis(2-phenylpropyl)siloxane | 10 | — | — |
| Stearyl alcohol | 19 | 19 | 19 |
| Hydrogenated castor oil | 3 | 3 | 3 |
| Talc | 4 | 4 | 4 |
| Glyceryl stearate and PEG-100 stearate | 2 | 2 | 2 |
| Aluminum zirconium chlohydex gly | 22 | 22 | 22 |
| Appearance on skin, | − | + | − |
| white residue visible (+) |  |  |  |
| no white residue visible (−) |  |  |  |

EXAMPLE 3 AND COMPARATIVE EXAMPLES C3 AND C4

The skin lotion compositions of Example 3 and Comparative Examples C3 and C4 were made by combining the components in the relative amounts, expressed in pbw, set forth below in Table II.

The compositions were made by (i) combining the components to from Part B and (ii) heating Part B to 70° C., (iii) combining the components to form Part A and heating Part A until melted, (iv) slowly adding molten Part A to Part B, (v) mixing the combined parts A and B for 30 minutes and (vi) cooling the mixture with continued mixing.

TABLE II

|  | 3 | C3 | C4 |
|---|---|---|---|
| Part A |  |  |  |
| Phenyltrimethicone | — | — | 3.6 |
| α,ω-bis(2-phenylpropyl)siloxane | 3.6 | — | — |
| stearic acid | 1.4 | 1.4 | 1.4 |
| cetyl alcohol | 1.0 | 1.0 | 1.0 |
| Part B |  |  |  |
| Glycerin | 2.0 | 2.0 | 2.0 |
| Triethanolamine | 0.8 | 0.8 | 0.8 |
| Methyl paraben | 0.15 | 0.15 | 0.15 |
| Deionized water | 91.05 | 94.65 | 91.05 |

The compositions of Example 3 and Comparative Examples C3 and C4 were applied to skin. Compared to the composition of Comparative Example C3, the compositions of Example 3 and Comparative Example C4 each felt less greasy and tacky during application, were rubbed into the skin faster and provided a more lubricious feel after drying.

EXAMPLE 4 AND COMPARATIVE EXAMPLES C5 AND C6

The after bath oil compositions of Example 4 and Comparative Examples C5 and C6 were made by combining the components in the relative amounts, expressed in pbw, set forth below in Table III. The silicone components were combined and mixed until homogeneous, the mineral oil was then added to the combined silicone components while mixing and mixing of the combined silicone components and mineral oil was continued for 15 minutes.

TABLE III

|  | 4 | C5 | C6 |
|---|---|---|---|
| Phenyltrimethicone | — | — | 10 |
| α,ω-bis(2-phenylpropyl)siloxane | 10 | — | — |
| cyclopentasiloxane | 58 | 58 | 58 |
| light mineral oil | 32 | 42 | 32 |

The after bath oil compositions of Example 4 and Comparative Examples C5 and C6 were each applied to skin. The composition of Comparative Example C5 dried quickly and did not provide a lubricious feel to the skin after drying. The composition of Comparative Example C6 took slightly longer to dry than did the composition of Comparative Example C5 and provided a soft, smooth and lubricious, but somewhat greasy feel to the skin after drying. The composition of Example 4 took slightly longer to dry than did the composition of Comparative Example C5 and provided a soft smooth and lubricious feel, which was less greasy than that provided by the composition of Comparative Example C6 to the skin after drying.

EXAMPLE 5 AND COMPARATIVE EXAMPLES C7 AND C8

The hair cuticle coating compositions of Example 5 and Comparative Examples C7 and C8 were made by combining the components in the relative amounts, expressed in pbw, set forth below in Table IV. The cyclomethicone, dimethicone and isohexadecane components were combined and the α,(ω-bis(2-phenylpropyl)siloxane or phenyltrimethicone was then added to the combined cyclomethicone, dimethicone and isohexadecane components with mixing and the mixing was continued for 15 minutes.

TABLE IV

|  | 5 | C7 | C8 |
|---|---|---|---|
| Cyclomethicone and dimethicone | 60 | 60 | 60 |
| Phenyltrimethicone | — | — | 30 |
| α,ω-bis(2-phenylpropyl)siloxane | 30 | — | — |
| isohexadecane | 10 | 40 | 10 |

The compositions of Example 5 and Comparative Examples C7 and C8 were applied to hair tresses. Each of the compositions initially provided shine and conditioning properties to the hair tresses. Upon drying, the tresses treated with composition of Comparative Example C7 exhibited a dull appearance, while those treated with the compositions of Example 5 and Comparative Example C8 continued to exhibit a shiny appearance.

What is claimed is:

1. A method of using of an aralkylsiloxane, comprising adding an aralkylsiloxane having the formula (I):

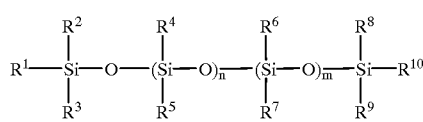

(I)

wherein:

$R^2$, $R^4$, and $R^5$ are each independently H, alkyl, haloalkyl, aryl or aralkyl, $R^6$, $R^7$ are each each ($C_1$–$C_{16}$)alkyl;

n and m are each independently integers from 0 to 6, provided that (n+m)≧1 and provided that at least one substituent group of the compound of formula (I) is aralkyl;

or of formula (II):

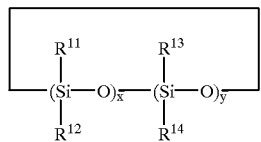

(II)

wherein:

$R^{11}$ and $R^{12}$ are each independently H, alkyl, haloalkyl, aryl or aralkyl;

$R^{13}$ and $R^{14}$ are each independently H, alkyl, haloalkyl or aryl;

x and y are each independently integers from 0 to 6, provided that 3≦(x+y)≦10 and provided that at least one substituent group of the compound of formula (II) is aralkyl where $R^1$ and $R^{10}$ are each aralkyl, $R^2$, $R^3$, $R^8$ and $R^9$ are each ($C_1$–$C_6$)alkyl, n is 0 and 2≦m≦5, said aralkylsiloxane being a component in a personal care composition, said composition comprising an inorganic component, in an amount effective to enhance one or more properties of the personal care composition selected from shine, emolliency, lubricity and visual masking of the inorganic component, wherein the relative amount of aralkyl substituent groups is selected to provide an aralkylsiloxane that exhibits a refractive index of from 1.40 to 1.50 at 25° C.

2. The method of claim 1, wherein the aralkylsiloxane comprises α,ω-bis(2-phenylpropyl)siloxane.

3. A personal care composition comprising an aralkylsiloxane having the formula (I):

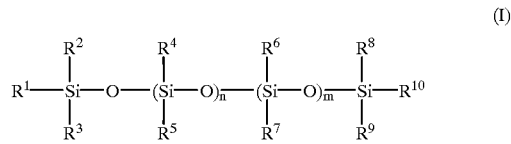

(I)

wherein:

$R^2$, $R^4$, and $R^5$ are each independently H, alkyl, haloalkyl, aryl or aralkyl, $R^6$, $R^7$ are each each ($C_1$–$C_6$) alkyl;

n and m are each independently integers from 0 to 6, provided that (n+m)≧1' and provided that at least one substituent group of the compound of formula (I) is aralkyl;

or of formula (II):

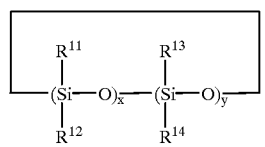

(II)

wherein:

$R^{11}$ and $R^{12}$ are each independently H, alkyl, haloalkyl, aryl or aralkyl;

$R^{13}$ and $R^{14}$ are each independently H, alkyl, haloalkyl or aryl;

x and y are each independently integers from 0 to 6, provided that 3≦(x+y)≦10 and provided that at least one substituent group of the compound of formula (II) is aralkyl where $R^1$ and $R^{10}$ are each aralkyl, $R^2$, $R^3$, $R^8$ and $R^9$ are each ($C_1$–$C_6$) alkyl, n is 0 and 2≦m≦5, said composition comprising an inorganic component, in an amount effective to enhance one or more properties of the personal care composition selected from shined, emolliency, lubricity and visual masking of the inorganic component, wherein the relative amount of aralkyl substituent groups is selected to provide an aralkylsiloxane that exhibits a refractive index of from 1.40 to 1.50 at 25° C.

4. The composition of claim 3, wherein the aralkylsiloxane comprises α,ω-bis(2-phenylpropyl)siloxane.

* * * * *